United States Patent [19]

Kawakami et al.

[11] Patent Number: 5,130,652
[45] Date of Patent: Jul. 14, 1992

[54] AC MAGNETIC FLUX LEAKAGE FLAW DETECTING APPARATUS FOR DETECTING FLAWS IN FLAT SURFACES WITH ROTATING LEAKAGE DETECTION ELEMENT

[75] Inventors: Masanobu Kawakami; Akio Kokubu, both of Tokyo, Japan

[73] Assignee: Eddio Corporation, Tokyo, Japan

[21] Appl. No.: 438,119

[22] Filed: Nov. 20, 1989

[30] Foreign Application Priority Data

Nov. 30, 1988 [JP] Japan ................... 63-302669

[51] Int. Cl.⁵ .................... G01N 27/90; G01R 33/12
[52] U.S. Cl. ........................... 324/240; 324/238
[58] Field of Search ............... 324/226, 236, 237, 238, 324/239, 240, 241, 242, 243

[56] References Cited

U.S. PATENT DOCUMENTS

| | | | |
|---|---|---|---|
| Re. 29,166 | 3/1977 | Forster | 324/241 |
| 2,617,854 | 11/1952 | Van Valkenburg | 324/240 |
| 3,281,667 | 10/1966 | Dobbins et al. | 324/241 |
| 3,588,682 | 6/1971 | Forster . | |
| 3,611,120 | 10/1971 | Forster | 324/37 |
| 4,297,636 | 10/1981 | Link et al. . | |
| 4,594,549 | 6/1986 | Smith et al. | 324/242 |
| 4,761,610 | 8/1988 | Svengander et al. | 324/240 |

OTHER PUBLICATIONS

General Dynamics, "Classroom Training Handbook, Non-Destructive Testing eddy current testing", 1967, pp. 2-1-2-15, (Reference A).

Beisnner, Matzkanin and Teller, "NDE Applications of Magnetic Leakage Field Methods" Jan. 1980, pp. 1-15 (Referemce B).

Primary Examiner—Walter E. Snow
Attorney, Agent, or Firm—Fleit, Jacobson, Cohn, Price, Holman & Stern

[57] ABSTRACT

An AC magnetic flux leakage type flaw detecting apparatus for use in flat surface flaw detecting comprises AC exciting means having a pair of magnetic poles for exciting a steel material to be flaw detected, a leakage magnetic flux detecting element, and rotatably scanning means for rotatably scanning the magnetic flux leakage detecting element in a surface substantially parallel to the flat surface oppositely to the flat surface to be flaw detected of the steel material in a plane of an exciting magnetic field between the pair of magnetic poles.

9 Claims, 6 Drawing Sheets

AC MAGNETIC FLUX LEAKAGE FLAW DETECTING APPARATUS FOR DETECTING FLAWS IN FLAT SURFACES WITH ROTATING LEAKAGE DETECTION ELEMENT

BACKGROUND OF THE INVENTION

1. Field of the Invention

This invention relates to a flaw detection of a steel material and, more particularly to an AC magnetic flux leakage type flaw detecting apparatus adapted to detect a flaw on a flat surface of a thick steel plate or an H-shaped steel.

2. Description of the Prior Art

As a non-destructive detecting method widely used in an inspection of a quality of a primary product of a steel plate, there are known certain methods such as an ultrasonic flaw detecting method, a magnetic flaw detecting method, an eddy current flaw detecting method, a magnetic flux leakage flaw detecting method, etc. According to the ultrasonic flaw detecting method and the magnetic flux leakage detecting method, there are problems that, since water, fluorescent magnetic powder/liquid are employed and an eye observation inspection are used, its low processing capacity and environmental pollution occur. The eddy current flaw detecting method has an excellent processing capacity due to fast detecting speed, but since it requires a magnetic saturation unit and a de magnetizing unit, the shape of the material to be detected is limited to a columnar or cylindrical shape, but it is scarcely applied to a flat surface of the plate except hot eddy current flaw detection exhibiting no ferromagnetism. Further, the leakage magnetic flux flaw detecting method is used to mainly detect a flaw of a round rod steel or steel pipe. This method detects a flaw by conveying a material to be detected of columnar or cylindrical shape while spirally rotating it on a turning roll, and disposing a sensor directly under the material to be detected. According to this method, the material to be detected is spirally rotated to detect the flaw on the entire surface. The whole surface of the material to be detected can also be flaw detected by linearly moving a round rod steel or a steel pipe by a conveyor and rotating an exciting yoke and a sensor along the outer periphery of the material to be detected. However, when the flaw of a square billet is intended to be detected, the material must be conveyed linearly. Thus, this method has such a disadvantage that the detecting region of the sensor must require the width at each surface of the billet and its detecting element must have multi-channels. Further, this method also has a defect that a flaw undetected range is generated on the ed of the outer periphery of the material to be detected.

As described above, the conventional steel material non-destructive detecting methods all have problems in the processing capacity or the environmental pollution, or in a relatively large scale due to the necessity of a magnetic saturation unit or a degaussing unit. Further, the material to be detected is limited to the columnar or cylindrical shape, and the conventional method is not adapted for detecting a flaw of the flat surface of the thick steel plate or the H-shaped steel and a thick plate welded portion. Thus, there is no conventional method which can defect a flaw of the thick steel plate or H-shaped steel by a simple mechanism without problems of the insufficient processing capacity and environmental pollution and without flaw undetected range. Generally, since side edges and its peripheries of the thick steel plate frequently suffer from defects due to rolling process, the necessity of detecting the defect is probably high, but according to the conventional magnetic flux leakage flaw detecting method, there are problems because undetected range exists at ends of the material to be detected and a linear flaw generated along the rolling or conveying direction frequently at the ends cannot be detected.

An object of this invention is to provide an AC magnetic flux leakage type flaw detecting apparatus for use in flat surface flaw detecting which can eliminate the above-described problems of the conventional art.

SUMMARY OF THE INVENTION

According to this invention, there is provided an AC magnetic flux leakage type flaw detecting apparatus for us in flat surface flaw detecting, comprising AC exciting means having a pair of magnetic poles for exciting a steel material to be flaw detected, a leakage magnetic flux detecting element, and a rotatable scanning means for rotatably scanning the magnetic flux leakage detecting element a plane or surface substantially parallel to the flat surface of said steel material to be flow detected in a between the pair of magnetic poles.

This invention will now be described in further detail with regard to preferred embodiments as illustrated in the accompanying drawings.

DESCRIPTION OF THE PREFERRED EMBODIMENTS

Figure 1:
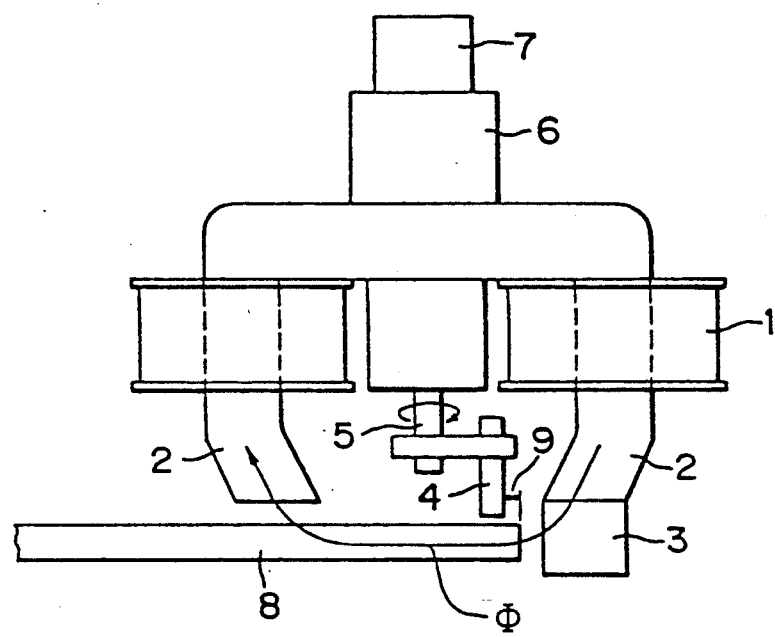
FIG. 1 is a schematic view showing the structure of an AC magnetic flux leakaqe type flaw detecting apparatus for use in flat surface flaw detecting as an embodiment of this invention.

As schematically shown in FIG. 1, an AC magnetic flux leakage type flaw detecting apparatus for use in flat surface flaw detecting according to this invention employs a magnetic flux leakage flaw detecting probe having 4 to 32 kHz AC to detect a crack or a flaw produced on the flat surface of a steel plate. This magnetic flux leakage flaw detecting probe essentially comprises a magnetic core having a pair of magnetic poles 2 and 2 wound with an AC exciting coil 1, and detecting coils 4 to be rotated around a driving shaft 5 between the pair of poles 2 and 2. The driving shaft 5 is rotatably driven by a motor 7. Thus, the detecting coils 4 are rotatably scanned in a plane opposite to and parallel to the upper surface of a material 8 to be detected between the pair of poles 2 and 2. The detecting coil 4 picks up a leakage magnetic flux generated when a surface flaw is provided with an exciting magnetic flux $\phi$ generated through the material 8 to be detected by the pair of poles 2 and 2 during the rotating scanning of the detecting coils 4. A detection signal of the detecting coils 4 is fed through a rotary transformer 6 to an external processor. The material 8 to be detected is of a thick steel plate or an H-shaped steel, and conveyed in this embodiment, for example, in a direction perpendicular to the paper in FIG. 1. Of course, a whole magnetic flux leakage flaw detecting probe may be moved in a directly perpendicular to the paper of FIG. 1.

In the embodiment shown in FIG. 1, in order to detect a flaw by reducing a flaw undetected region as much as possible on the upper face of the edge of the material 8 to be detected, a pole attachment 3 for forming a magnetic circuit of a silicon steel plate of the like to the right side pole 2. With such an attachment 3 provided, an exciting magnetic path can be extended to the corners of the steel plate, and the flaw undetected region can be suppressed to a minimum value as designated by reference numeral 9. This is adapted to detect a crack flaw of a longitudinal direction generated at the end of an abnormal shape material, and also adapted to detect the flaw on the flat surface of the H-shaped steel or a square billet or its side end.

Figure 2:
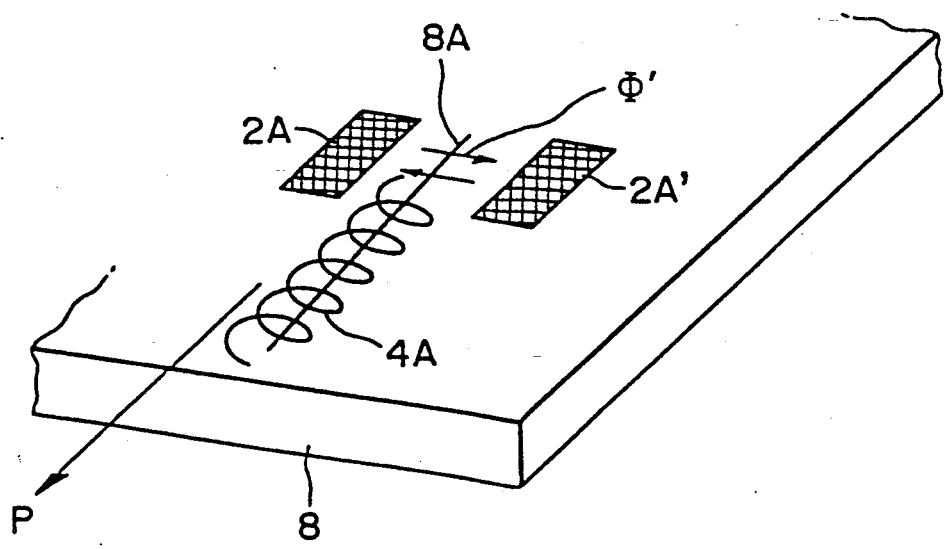
FIG. 2 is a view schematically showing a scanning locus of a detecting coil when a flaw of not the upper surface of the edge of a material to be detected but the upper surface of the intermediate portion isolated from the edge of the material to be detected is detected by the flaw detector of FIG. 1.

FIG. 2 schematically shows a scanning locus of the detecting coils 4 when not the upper surface of the edge of the material 8 to be detected but the upper surface of the intermediate portion isolated from the edge of the material 8 to be detected is flaw detected by the flaw detected of FIG. 1. In FIG. 2, reference symbols 2A and 2A' denote the projecting shades of magnetic coupling opposite faces of a pair of poles 2 and 2 in which the attachment 3 is not fitted, symbol 8A denotes a linear flow of a rolling direction presented on the upper surface of the material 8 to be detected, symbol P denotes the scanning or conveying direction of the material 8 to be detected, symbol 4A denotes the turning scanning locus of the detecting coils 4, and symbol $\phi'$ denotes lines of alternating exciting magnetic force of the pair of poles 2 and 2. In this manner, the line of alternating exciting magnetic force $\phi'$ is generated, for example, by applying an AC current having 8 kHz of frequency to the exciting coil 1. Crack flaws produced in the steel plate of the material 8 to be detected are frequently distributed in a direction of 0±45° with respect to the rolling direction, in a direction crossing the above-mentioned lines of exciting magnetic force.

Figure 3:
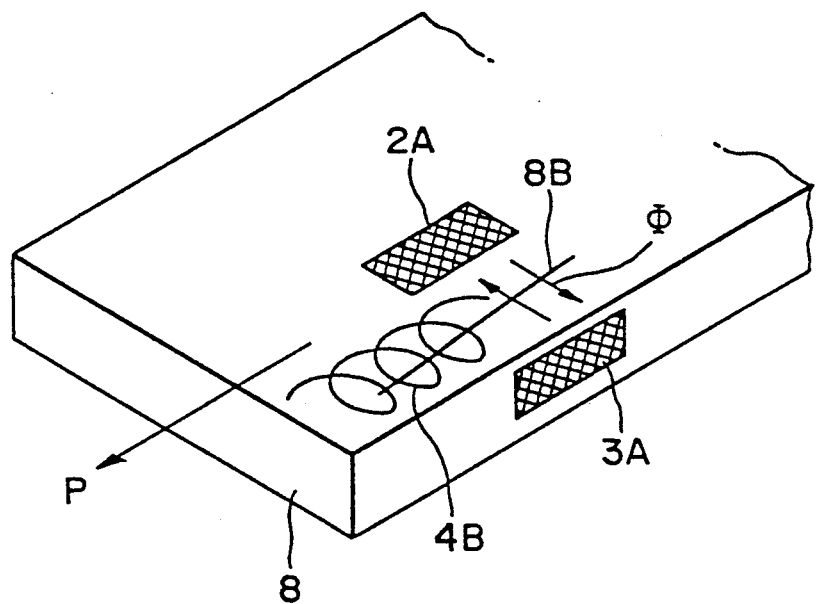
FIG. 3 is a view schematically showing a scanning locus of the detecting coil when the upper surface of the edge of the material to be detected is detected by the flaw detector of FIG. 1.

FIG. 3 schematically shows the scanning locus of the detecting coils 4 when the flaw of the upper surface of the edge of the material 8 to be detected is detected by the flaw detector of FIG. 1. In FIG. 3, reference symbol 2A denotes the shade of the magnetic coupling opposite face of the pole 2 of the left side of a pair of poles 2 and 2, symbol 3A denotes the shade of the magnetic coupling opposite face of the pole 2 of the right side in which an attachment 3 is fitted, symbol 8B denotes a linear flaw of a rolling direction presented on the upper surface of the edge of the material 8 to be detected, symbol P denotes a scanning or conveying direction of the material 8 to be detected, symbol 4B denotes a turning scanning locus of the detecting coils 4, and symbol $\phi$ denotes the lines of alternating exciting magnetic force of a pair of poles 2, 2 and 3.

The detecting coils 4 are differentially connected at two coils adjacent to the elevational direction or rotatably circumferentially rightward or leftward in such a manner that the directions of the coils are perpendicular to the surface of the steel plate of the material to be detected and crosses perpendicularly the parallel magnetic flux leakage in the flat surface space. When the probe is scanned on the steel plate and a crack flaw exists on the flat surface between the exciting poles 2 and 2, a magnetic flux leakage generated from the crack flaw crosses the detecting coils 4 to generate an induced voltage in the coils, thereby detecting the flaw. A lift off signal due to the vibration of the steel plate is of an induced voltage of a parallel magnetic field on the surface of the steel plate. Since it has largely different phase from that of the induced voltage due to the magnetic flux leakage generated from the crack flaw, an unnecessary signal can be easily removed by a phase analysis of a processor or the like as will be described later, thereby providing an excellent S/N ratio.

As a magnetic flux leakage detecting element, semiconductor elements such as Hall elements of SMDs or the like may be used by similarly differentially connecting them instead of the above-mentioned detecting coils. In this case, when two elements are disposed adjacently along the flat surface of the steel plate, a flaw cannot be detected when the detecting element rotated on the flat surface becomes parallel to the crack flaw, and its directionality is therefore needed to be noted.

Figure 4:
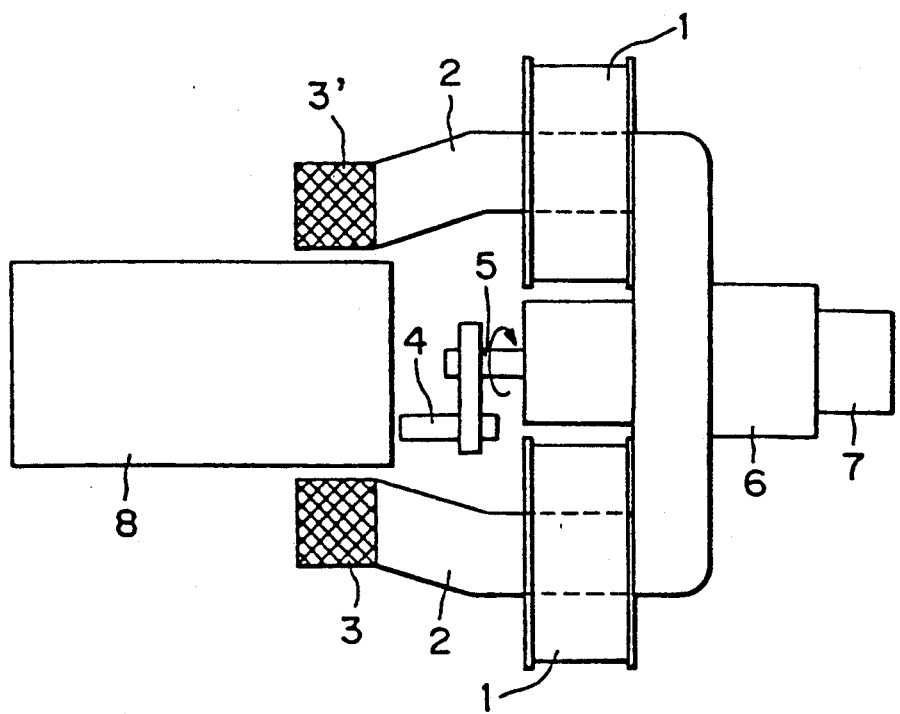
FIG. 4 is a schematic view showing another embodiment of the detector of this invention.
Figure 5:
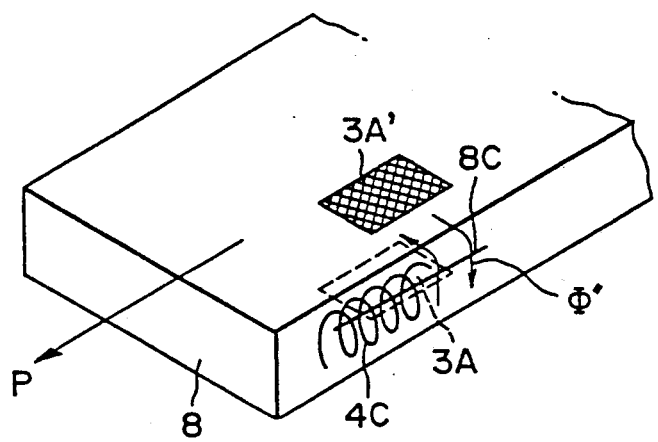
FIG. 5 is a view schematically showing a scanning locus of the detecting coil when the flaw of the end face of the edge of the material to be detected is detected by the detector of FIG. 4.

FIG. 4 schematically shows another embodiment of a flaw detector of this invention. The flaw detector of the embodiment in FIG. 4 has mostly the same arrangement as that of the flaw detector of FIG. 1, and only the different constitution will be described. The flaw detector of this embodiment is constructed to flaw detect the end face of the edge of the steel plate 8 of the material to be detected. Pole attachments 3 and 3' are respectively mounted on poles 2 and 2, and so arranged as to oppose the upper and lower surfaces of the edge of the steel plate 8. A detecting coil 4 is rotated around a driving shaft 5 to rotatably scan the end face of the edge of the steel plate 8, thereby detecting a flaw presented on the end face. FIG. 5 schematically shows the scanning locus of a detecting coil 4 when the end face of the edge of the material 8 to be detected is flaw detected. In FIG. 5, reference symbols 3A and 3A' denote the shades of magnetic coupling opposite faces of a pair of pole attachments 3 and 3', symbol 8C denotes a linear flaw of a rolling direction presented on the end face of the edge of the material 8 to be detected, symbol P denotes a scanning or conveying direction of the material 8 to be detected, symbol 4C denotes the turning scanning locus of the detecting coil 4, and symbol $\phi$ denotes lines of alternating exciting magnetic force of the pair of pole attachments 3 and 3'.

In the embodiment in FIG. 4, it is necessary to suitably set an applying alternating frequency of generating an AC magnetic flux leakage so that an exciting magnetic field formed between the pole attachments 3 and 3' is not fed at the shortest distance between the pole attachments 3 and 3'. In order to form the exciting magnetic field formed along the vicinity of the end face of the edge of the steel plate 8 like the exciting magnetic flux $\phi''$ shown in FIG. 5, it is preferable to set the applying alternating frequency to 16 $KH_z$ or the like much higher than 4 $KH_z$. Such use of higher frequency of applied alternating magnetic field would cause alternating magnetic flux flowing into a steel material to tend to be concentrated on the surface of the steel material so that magnetic flux may pass through the outer surface layer of the steel material, which would result in high magnetization at the surface layer of side edges of the steel material.

Figure 6:
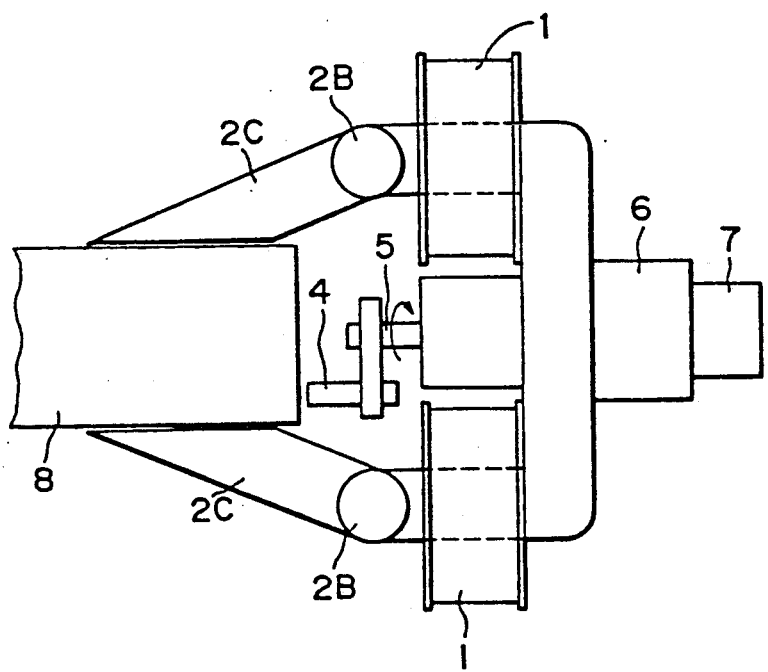
FIG. 6 is a schematic view showing a further modified embodiment of a flaw detector of FIG. 4.

FIG. 6 schematically shows a further modified embodiment of the flaw detector of FIG. 4. Since this embodiment has substantially the same arrangement as that of the flaw detector of FIG. 4, and only different components will be therefore described. This embodiment has a similar structure to a movable openable/closable pole structure used to hold the application outer diameter range wide in the magnetic powder flaw detection or the flaw detection of a round rod steel by an AC magnetic flux leakage flaw detecting method. In this embodiment, a pair of poles 2C and 2C are so respectively rotated at pivots 2B and 2B as centers as to detect a flaw in the steel plate 8 of the material to be detected having various different thicknesses.

The example of detecting the flaw as described with respect to FIG. 3 is adapted to detect a linear flaw of rolling or conveying direction generated at the periphery of the edge of the material to be detected, and to be frequently used to defect flaws at the corners of a square billet or a stripe steel.

The example of detecting the flaw as described with respect to FIG. 5 is adapted to detect a linear flaw of a thermally affected portion near a rolling conveying or welding line generated on the end face of the edge of the material to be detected. This method can not only provide the same advantages as those of the flaw detection described with respect to FIG. 2, but eliminate the insufficient magnetization of the periphery of a flaw if the poles are not disposed near the flaw to be detected like an AC magnetic powder/magnetic flaw detection using a DC or a low frequency such as 50 to 60 Hz.

The above-described signal transmitting noncontact rotary transformer 6 may be replaced with the combination of a slip ring and a brush by mechanical contact.

In the conventional method, the same scanning locus as a probe scanning locus shown in FIG. 2 is performed by an electromagnetic induction (eddy current) flaw detection. Accordingly, it was impossible to detect a small flaw with good S/N ration in a state immediately after a hot rolling having wrong surface skin. In order to overcome this defect, it has been proposed to locally employ together with a DC magnetic saturation, but there are still problems of adverse influence of DC magnetism, i.e., demagnetizing after flaw detection and adherecne of iron powder to the periphery of the pole and generation of a false-signal due to the adherence, removal and floating of the iron powder. According to this invention, such difficulties can not be only overcome, but there are provided advantages that substantially constant detecting capacity is maintained irrespective of the static or dynamic sensor assembly (exciting poles, rotary probe, probe rotatably driving mechanism and signal transmitting rotary transformer) by always dynamically and mechanically holding substantially constantly a gap between the probe and the surface of the material to be detected to be rotated for an object to be detected such as an existing facility structure, for example, welded building, a fixed tank and any means such as clamping and disposing the flaw detector of this invention at every detection or movement at an arbitrary speed according to the principle in which a flaw signal detection must be performed by the differential operation of the dynamic relative motion of the detector in a conventional eddy current flaw detection and AC leakage magnetic flux flaw detection.

Figure 7:
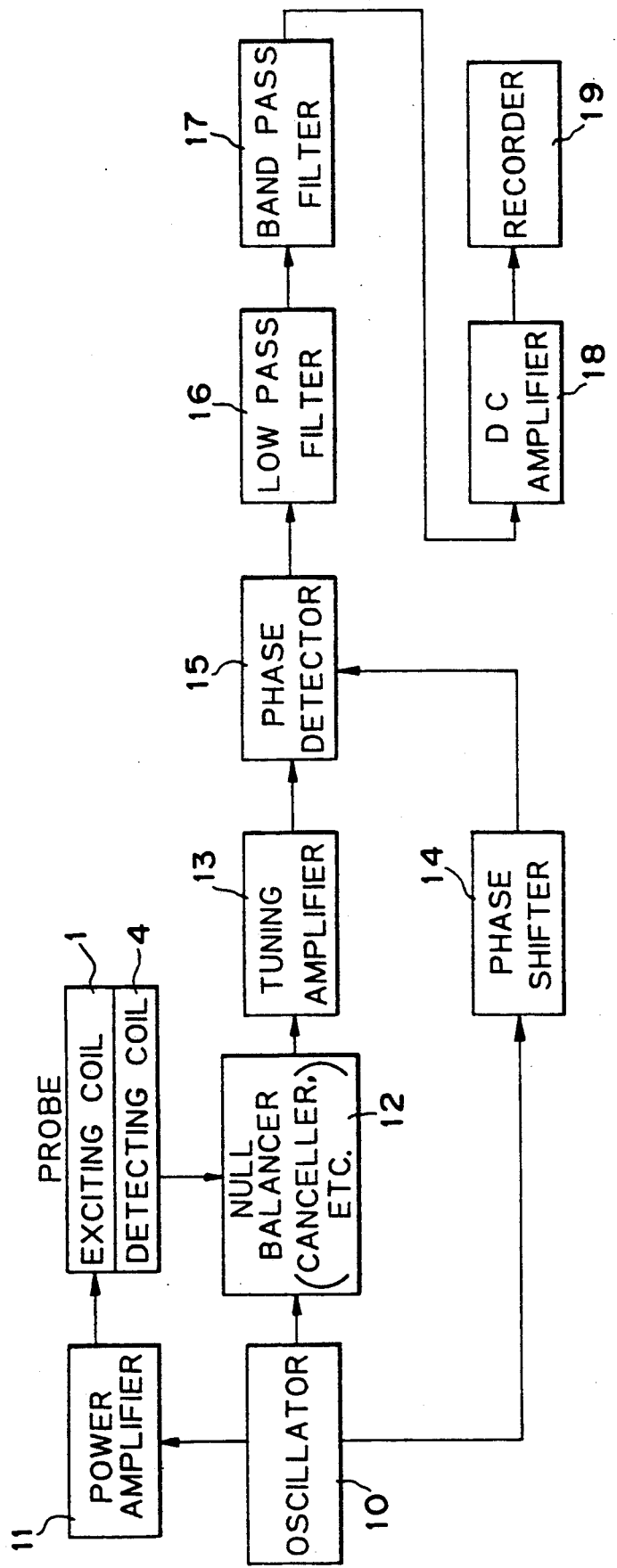
FIG. 7 is a block diagram showing an arrangement of an embodiment of a power source processor for energizing the signal detected by the exciting coil and processing a signal detected by the detecting coil of the flaw detector of this invention.

FIG. 7 is a block diagram showing an arrangement of an embodiment of a signal processor for processing a signal to be detected by energizing the exciting coil and the detecting coils of the flaw detector of this invention. According to this signal processor, an oscillation output of an oscillator 10 as a power source is applied through a power amplifier 11 to the exciting coil 1 to excite the material to be detected. The signal from the detecting coil 4 is amplified through a balancer 12 by a tuning amplifier 13, and fed to a phase detector 15. The oscillation output from the oscillator 10 is input through a phase shifter 14 to the phase detector 15. The output of the phase detector 15 is input through a low pass filter 16, a band pass filter 17 and a DC amplifier 18 to a recorder 19 which records a detected flaw signal.

Figure 10:
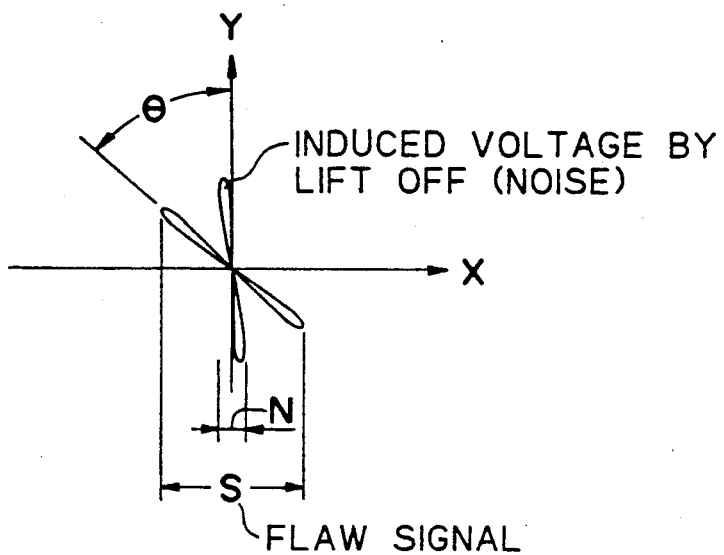
FIG. 10 is a view showing quadrature phase-detected output to explain the phase relationship between the flaw signal and the induced voltage unnecessary noise signal due to lift off.

The phase difference between the flaw signal detected by the detecting coil 4 and an induced voltage unnecessary noise signal due to the lift off of the material to be detected was approx. 50°. Accordingly, as shown in FIG. 10, when the induced voltage unnecessary noise signal due to the lift off is phase-regulated by the phase shifter 14 as shown on the Y axis of X-Y coordinates and the circuit is so composed as to output a signal from the X-axis of the output of the phase detector 15, a projecting vector amount S is extracted as a flaw signal, and the projecting vector amount N with respect to the X-axis of the unnecessary noise signal showing the Y-axis direction becomes small. Namely, in FIG. 10, reference character $\theta$ indicates the phase difference between the flaw signal and the voltage induced by lift-off or undesired noisy signal (noise), reference character S indicates a vector of the flaw signal projected onto the X-axis, and reference character N indicates a vector of the noise projected onto the X-axis. More specifically, according to the circuit arrangement of FIG. 7, the amplitude values are inverted by the relation of the flaw signal amplitude < the induced voltage unnecessary noise signal amplitude due to the lift off as shown in sketch diagram of the real flaw detector phase detection output two-dimensional display in FIG. 10, and the flaw detection result of good S/N ratio is obtained.

Figure 8:
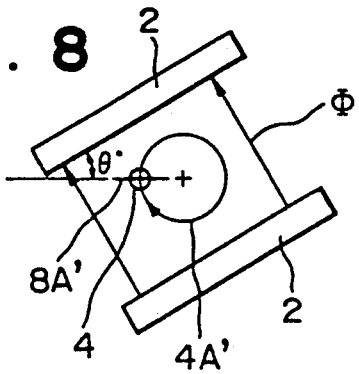
FIG. 8 is an explanatory view for use in explaining about the directionality as measured while the relative angle between the exciting magnetic pole and the extending direction of an artificial flaw formed on the surface of the material to be detected by the flaw detector of FIG. 1 is changed.
Figure 9:
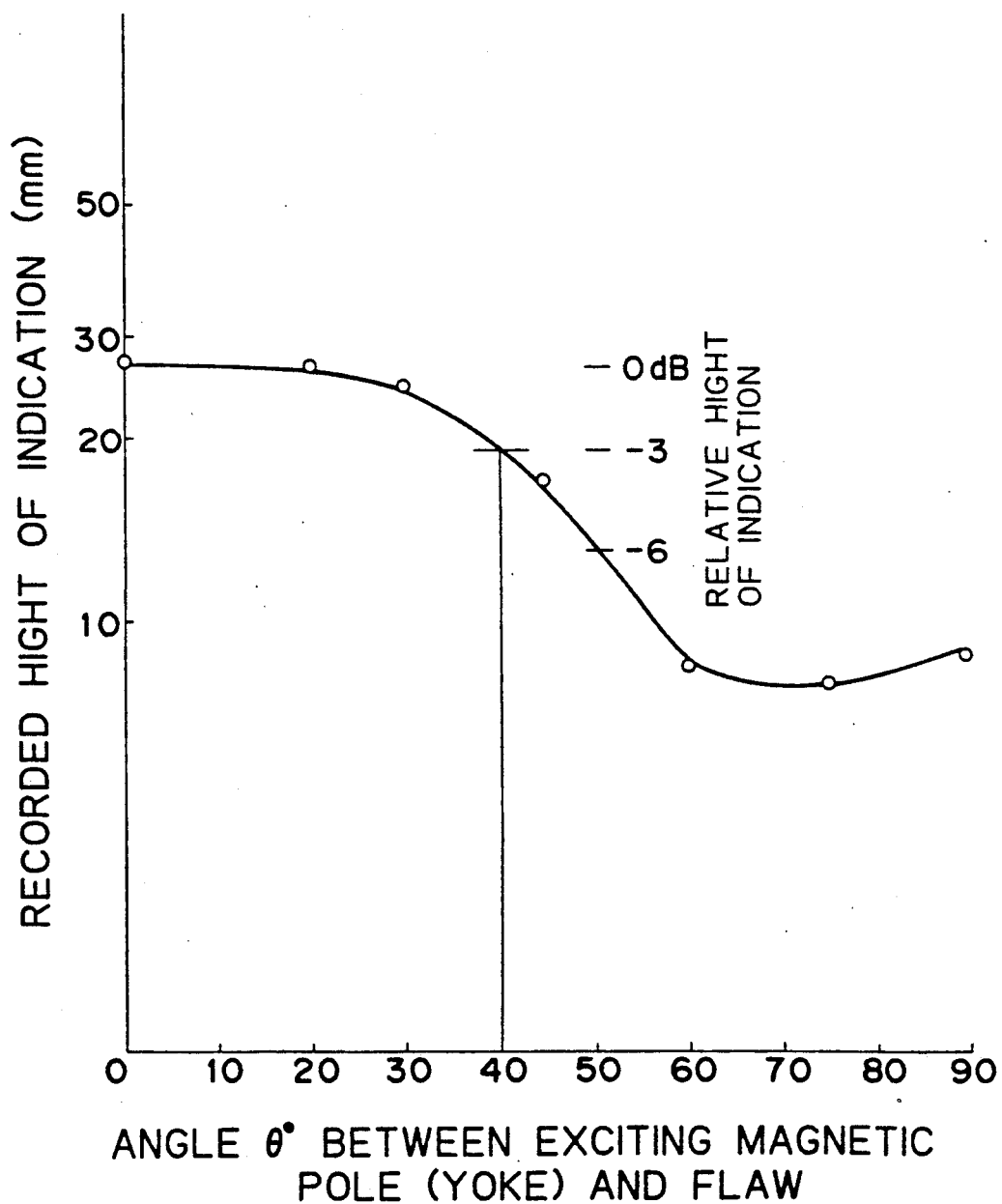
FIG. 9 is a graph showing the results of measurement of the directionality.

In order to further examine the optimum positional relationship between the flaw to be detected by the flaw detector of this invention and the exciting poles, as shown in FIG. 8, the directionality was measured while the relative angle θ° between the exciting pole 2 and the extending direction of an artificial flaw 8A' formed on the surface of the material to be detected is altered. In FIG. 8, symbol φ' denotes an exciting magnetic flux formed between the exciting poles 2 and 2, and symbol 4A' denotes the rotating direction of the detecting coil 4. The measured result is quantized and shown in FIG. 9. FIG. 9 shows the relationship between the angle θ between the exciting poles and the artificial flaw and the recording designation height when the artificial flaw has 0.2 mm of depth, 0.1 mm of width and 10 mm of length. As understood from the curve of FIG. 9, if the angle θ falls within the range of 0° to approx. ±40°, it falls within the sensitivity of −3 dB. More particularly, it is understood that a linear flaw in a range of ±45° from the rolling direction of the steel material can be sufficiently detected.

Figure 11:
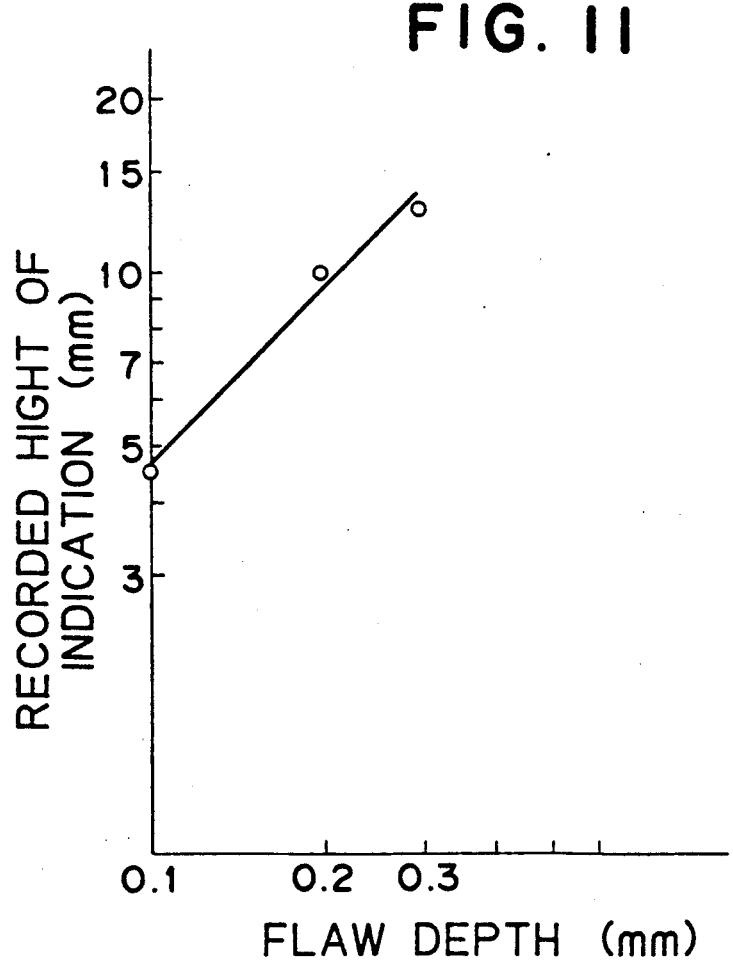
FIG. 11 is a view showing the relationship between the depth of the flaw and the signal designation height of the flaw detection result.

Further, the relationship between the depth of the flaw and the signal designation height of the flaw detection result is shown in FIG. 11. As understood from the curve of FIG. 11, the relationship has a substantial linearity, and if the designation height is calibrated in advance by an artificial flaw having an apparent depth of the flaw, the depth of natural flaw can be presumed.

The interval between the magnetic coupling opposite face of the exciting pole and the material to be detected is so mechanically coped as to hold a noncontact state of the value of approx. 4 to 10 mm.

According to the AC magnetic flux leakage type flaw detecting apparatus for use in flat surface flaw detecting of this invention, as described above, the flaw detection of the flat surface of the thick steel plate or the H-shaped steel and both side faces thereof which was impossible to be detected can be performed by suppressing the flaw undetected range to the minimum limit by a very simple arrangement of rotatably scanning a magnetic flux leakage detecting element in the flat surface of the exciting magnetic field to be formed between the AC exciting poles, and the flaw detecting capacity can be improved.

Further, according to this invention, the flaw of not only the upper and lower surfaces of the material to be detected but the end face of the edge of the material to be detected can be easily detected, and the lift off false signal detection at the end of the sensor can be easily eliminated, and the suppressing control operation of the complicated end effect false signal can be readily obviated.

What is claimed is:

1. An AC magnetic flux leakage flaw detecting apparatus for use in flat surface flaw detecting, comprising:
   AC exciting means having a pair of magnetic poles for generating an exciting magnetic field therebetween and in proximity with a flat surface of a steel material to be scanned for flaws;
   a leakage magnetic flux detecting element; and
   rotating means for rotatably scanning said leakage magnetic flux detecting element in a plane of rotation which is substantially parallel to and opposite said flat surface of the steel material under detection, said plane of rotation being positioned between said pair of magnetic poles.

2. An AC magnetic flux leakage flaw detecting apparatus as defined in claim 1, wherein said pair of magnetic poles are disposed opposite and in proximity with an upper or lower flat surface of said steel material to be scanned so that the upper or lower surface can be scanned.

3. An AC magnetic flux leakage flaw detecting apparatus as defined in claim 1, wherein a first of said magnetic poles is disposed opposite and in proximity with an upper or lower flat surface of said steel material, and a second of said magnetic poles is disposed opposite and in proximity with an end face of said said steel material which is perpendicular to said upper or lower flat surface so that said upper or lower flat surface can be scanned by said leakage magnetic flux detecting element.

4. An AC magnetic flux leakage flaw detecting apparatus as defined in claim 1, wherein a first of said pair of magnetic poles is disposed opposite and in proximity with an upper surface of said steel material and a second of said magnetic poles is disposed opposite and in proximity with a lower surface of said steel material so that an end face perpendicular to and terminating said upper and lower surfaces is scanned by said leakage magnetic flux scanning element.

5. An AC magnetic flux leakage flaw detecting apparatus for use in flat surface flaw detecting, comprising:
   AC exciting means having a pair of magnetic poles for generating an exciting magnetic field therebetween and in proximity with a flat surface of a steel material to be flaw detected, wherein a first one of said magnetic poles is disposed opposite and in proximity with an upper or lower flat surface of said steel material and a second of said pair of magnetic poles being disposed opposite and in proximity with an end face of said steel material which is perpendicular to said upper or lower flat surface;
   a leakage magnetic flux detecting element; and
   rotating means for rotatably scanning said leakage magnetic flux detecting element in a plane of rotation which is substantially parallel to and opposite said upper or lower flat surface for detecting flaws in said upper or lower flat surface, said plane of rotation being between said pair of magnetic poles.

6. An AC magnetic flux leakage type flaw detecting apparatus for use in flat surface flaw detecting, comprising:
   AC exciting means having a pair of magnetic poles for generating an exciting magnetic field therebetween and in proximity with a flat surface of a steel material to be flaw detected, wherein a first of said pair of magnetic poles is disposed opposite and in proximity with an upper surface of said steel material and a second of said pair of magnetic poles is disposed opposite and in .proximity with a lower surface of said steel material;
   a leakage magnetic flux detecting element; and
   rotating means for rotatably scanning said leakage magnetic flux detecting element in a plane of rotation which is substantially parallel to and opposite said flat surface of the steel material, said flat end surface being perpendicular to and terminating said upper and lower surfaces, and said plane of rotation being positioned between said pair of magnetic poles.

7. An AC magnetic flux leakage type flaw detecting apparatus as defined in claim 6, wherein the exciting frequency of said AC exciting means is 4 to 32 kHz.

8. The AC magnetic flux leakage flaw detecting apparatus as defined in claim 1, and further comprising:
   oscillator means for generating an oscillating output;
   power amplifier means connected to said AC exciting means for amplifying said oscillating output and supplying said amplifying output to drive said AC exciting means;

balancing means connected to said leakage magnetic flux detecting element;

tuning amplifying means connected to said balancing means for amplifying signals detected by said leakage magnetic flux detecting element;

phase detector means connected to said tuning amplifier means;

phase shifter means connected to said oscillator means and to said phase detector means for supplying said oscillating output to said phase detector means through said phase shifter means;

low pass filter means connected to said phase detector means for filtering the output of said phase detector means;

band pass filter means connected to said phase detector means for filtering the output of said low pass filter means; and DC amplifier means for amplifying the output of said band pass filter means for generating a flaw detection signal.

9. The AC magnetic flux leakage flaw detecting apparatus of claim 1, wherein said leakage material flux detecting element picks up a leakage magnetic flux in said magnetic field caused by a surface flaw in said flat surface.

* * * * *